United States Patent
Pullela et al.

(10) Patent No.: US 12,195,480 B2
(45) Date of Patent: Jan. 14, 2025

(54) POLYMORPHS OF INTEGRASE INHIBITOR

(71) Applicant: CIPLA LIMITED, Maharashtra (IN)

(72) Inventors: Venkata Srinivas Pullela, Bangalore (IN); Srinivas Laxminarayan Pathi, Bangalore (IN); Ramanaiah Chennuru, Nellore(Dt) Andhra Pradesh (IN); Manjinder Singh Phull, Mumbai (IN); Anjaneyaraju Indukari, Hyderabad (IN)

(73) Assignee: Cipla Limited, Maharashtra (IN)

( * ) Notice: Subject to any disclaimer, the term of this patent is extended or adjusted under 35 U.S.C. 154(b) by 799 days.

(21) Appl. No.: 17/429,438

(22) PCT Filed: Feb. 6, 2020

(86) PCT No.: PCT/IN2020/050118
§ 371 (c)(1),
(2) Date: Aug. 9, 2021

(87) PCT Pub. No.: WO2020/161744
PCT Pub. Date: Aug. 13, 2020

(65) Prior Publication Data
US 2022/0144851 A1 May 12, 2022

(30) Foreign Application Priority Data

Feb. 7, 2019 (IN) .............................. 201921004899
Apr. 11, 2019 (IN) .............................. 201921014673

(51) Int. Cl.
*C07D 498/14* (2006.01)

(52) U.S. Cl.
CPC ........ *C07D 498/14* (2013.01); *C07B 2200/13* (2013.01)

(58) Field of Classification Search
CPC ......................... C07D 498/14; C07B 2200/13
See application file for complete search history.

(56) References Cited

FOREIGN PATENT DOCUMENTS

| WO | 2015/196116 A1 | 12/2015 |
|---|---|---|
| WO | 2018/229798 A1 | 12/2018 |

OTHER PUBLICATIONS

International Search Report and Written Opinion issued in PCT/IN2020/050118, dated Apr. 27, 2020, 11 pages.
Mino R Caira Ed—Montchamp Jean-Luc, "Crystalline Polymorphism of Organic Compounds", Jan. 1, 1998 (Jan. 1, 1998), vol. 198, p. 163-208.

*Primary Examiner* — Susanna Moore
*Assistant Examiner* — Luisalberto Gonzalez
(74) *Attorney, Agent, or Firm* — Meunier Carlin & Curfman LLC (57) ABSTRACT

Novel crystalline forms of Bictegravir sodium, pharmaceutical compositions containing said crystalline forms and the use of said crystalline forms in the treatment of HIV infection are disclosed. The present invention is further directed to the processes for the preparation of the novel crystalline forms.

10 Claims, 7 Drawing Sheets

Figure-1: PXRD of Form-C2

Figure-2: PXRD of Form-C3

Figure-3: PXRD of Form-C4

Figure-4: PXRD of Form-C5

Figure-5: DSC of Form-C4

Figure-6:TGA of Form-C4

Figure-7: DVS of Form-C4

Figure-8: PXRD of Form-C6

Figure-9: PXRD of Form-C7

Figure-10: PXRD of Form-C8

Figure-11: PXRD of Form-C9

POLYMORPHS OF INTEGRASE INHIBITOR

TECHNICAL FIELD OF THE INVENTION

The present invention relates to novel polymorphic forms of (2R,5S,13Ar)-8-hydroxy-7,9-dioxo-N-(2,4,6-trifluorobenzyl)-2,3,4,5,7,9,13,13a-octahydro-2,5-methanopyrido [1',2':4,5] pyrazino [2,1-b][1,3]oxazepine-10-catboxamide or its pharmaceutically acceptable salts and process for synthesis of novel polymorphic forms of (2R,5S,13Ar)-8-hydroxy-7,9-dioxo-N-(2,4,6-trifluorobenzyl)-2,3,4,5,7,9,13, 13a-octahydro-2,5-methanopyrido [1',2':4,5]pyrazino [2,1-b][1,3]oxazepine-10-catboxamide or its pharmaceutically acceptable salts.

BACKGROUND OF THE INVENTION (2R,5S,13aR)-8-hydroxy-7,9-dioxo-N-(2,4,6-trifluorobenzyl)-2,3,4,5,7,9,13,13a-octahydro-2,5-methanopyrido [1',2':4,5] pyrazino [2,1-b][1,3]oxazepine-10-catboxamide is also known as Bictegravir (I).

(I)

Bictegravir or its pharmaceutically acceptable salts is an HIV integrase inhibitor which is used to inhibit the activity of HIV integrase and used to reduce HIV replication and thus to treat HIV infections.

Bictegravir is currently filed at USFDA by Gilead, in combination with Emtricitabine and Tenofovir alafenamide for treatment of HIV.

Bictegravir belongs to class of polycyclic carbamoylpyridone compounds and is disclosed in WO2014100323. This patent application also discloses process for preparation of Bictegravir.

WO2015196137 claims polymorphic forms I, II, III, IV, V, VI, VII & VIII of Bictegravir; cocrystals of Bictegravir with fumaric acid, citric acid, oxalic acid; polymorphic forms I, II & III of Bictegravir potassium.

WO2015196116 claims sodium salt of Bictegravir which further claims crystalline form I of sodium salt of Bictegravir.

It is a well-known fact that different polymorphic forms of the same drug may have substantial differences in certain pharmaceutically-important physicochemical properties, such as stability, solubility, dissolution rate, crystal habit, tableting behaviour. Changes in certain of these physiochemical properties may ultimately affect the bioavailability of the drug. Furthermore, different physical forms may have different particle size, hardness and glass transition temperatures. In certain cases, this phenomenon may affect the quality and performance of the final dosage form.

Thus, there is a need in the art for polymorphic forms of Bictegravir or its pharmaceutically acceptable salts.

OBJECT OF THE INVENTION

It is an object of the present invention to provide novel polymorphs of Bictegravir or its pharmaceutically acceptable salts.

It is another object of the present invention to provide processes for the preparation of novel polymorphs of Bictegravir or its pharmaceutically acceptable salts.

It is further object of this invention to provide a pharmaceutical composition comprising novel polymorphs of Bictegravir or its pharmaceutically acceptable salts and pharmaceutically acceptable carrier, diluent or excipients.

It is another object of this invention to use pharmaceutical composition defined hereinabove for the treatment of HIV infections.

SUMMARY OF THE INVENTION

In one embodiment, the invention encompasses novel polymorphs of Bictegravir or its pharmaceutically acceptable salts.

More preferably, the invention encompasses crystalline forms of Bictegravir sodium hereinafter referred to as Form-C2, Form-C3, Form-C4 Form-C5, Form-C6, Form-C7, Form-C8, and Form-C9.

The crystalline form of Bictegravir sodium may be in a pseudo polymorphic form.

Accordingly, pseudo polymorphs provided include hydrates and/or solvates.

The crystalline nature of forms according to the present invention is characterized by X-ray powder diffraction pattern.

In another embodiment, the invention encompasses processes for the preparation of crystalline forms of Bictegravir sodium.

The present invention further provides pharmaceutical compositions containing novel crystalline forms of Bictegravir sodium.

The invention also provides methods of treatment of diseases or symptoms wherein Bictegravir is useful. In particular, the invention encompasses novel crystalline forms of Bictegravir sodium for use in methods of treating or prophylactically preventing an HIV infection.

In yet another embodiment, the invention encompasses the use of novel crystalline forms of Bictegravir sodium in the manufacture of medicament for treating or prophylactically preventing an HIV infection.

DETAILED DESCRIPTION OF THE INVENTION

Unless defined otherwise, technical and scientific terms used herein have the same meaning as commonly understood by one of ordinary skill in the art to which this invention belongs, and are consistent with:

Definitions

"Polymorph", as used herein, refers to the occurrence of different crystalline forms of a compound. Crystalline forms have different arrangements and/or conformations of the molecule in the crystal lattice. Solvates are crystal forms containing either stoichiometric or nonstoichiometric amounts of a solvent. If the incorporated solvent is water, the solvate is commonly known as a hydrate. Therefore, a single compound may give rise to a variety of polymorphic forms where each form has different and distinct physical properties, such as solubility profiles, melting point temperatures, hygroscopicity, particle shape, density, flowability, compactability and/or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form.

A crystalline solid substance is characterized by a regular three dimensional arrangement of atoms due to which they have well defined geometrical shape. On the other hand, amorphous solid substances do not exhibit this arrangement. Thus, compared to crystalline solid substances, amorphous solid substances have a different internal structure and a larger surface area, and therefore they exhibit a higher solubility. If the solubility and bioavailability of pharmaceutically active substances needs to be increased, they are preferably prepared in an amorphous form.

As used herein, the term "PXRD" refers to powder X-ray diffraction, the term "IR" refers to infrared, the term "NMR" refers to nuclear magnetic resonance, the term "TGA" refers to thermogravimetric analysis, the term "DSC" refers to differential scanning calorimetry and the term "DVS" refers to dynamic vapour sorption isotherm.

As used herein, the term "substantially the same X-ray powder diffraction pattern" is understood to mean that those X-ray powder diffraction patterns having diffraction peaks with 2θ values within ±0.2° of the diffraction pattern referred to herein are within the scope of the referred to diffraction pattern.

As used herein, the term "solvate" refers to an association or complex of one or more solvent molecules and a compound of the invention. Such solvents for the invention may not interfere with the biological activity of the solute. Typically, the solvent used is a pharmaceutically acceptable solvent. Examples of solvents that form solvates include, but are not limited to, C1-C4 alcohol solvents such as isopropanol, ethanol, methanol, butanol, aromatic alcohols such as benzyl alcohol, phenethyl alcohol; esters such as methyl benzoate, methyl acetate, ethyl acetate; nitriles such as acetonitrile; chlorinated solvents such as dichloromethane; ethers such as tetrahydrofuran (THF), diethyl ether, dimethyl ether and ketones such as acetone, other than water at levels of more than 1%.

The solvate can be isolated either as an amorphous form or in a crystalline form, preferably in crystalline form.

The solvate can be further isolated either in anhydrous form or hydrated form.

As used herein, the term "hydrate" refers to the complex where the solvent molecule is water. The skilled person will appreciate that the water molecules are absorbed, adsorbed or contained within a crystal lattice of the solid compounds, usually in defined stoichiometric ratio. The notation for a hydrated compound may be. $nH_2O$, where n is the number of water molecules per formula unit of the compound. For example, in a hemihydrate, n is 0.5; in a monohydrate n is one; in a sesquihydrate, n is 1.5; in a dihydrate, n is 2; and so on.

The novel polymorphs of the present invention may be isolated in pseudo polymorphic form as a solvate optionally in hydrated form, or as a non-hydrated solvate.

As polymorphic forms are reliably characterized by peak positions in the X-ray diffractogram, the polymorphs of the present invention have been characterized by powder X-ray diffraction spectroscopy which produces a fingerprint of the crystalline form and is able to distinguish it from all other crystalline and amorphous forms of Bictegravir sodium. Measurements of 2θ values are accurate to within ±0.2 degrees. All the powder diffraction patterns were measured on a PANalytical X'Pert[3] X-ray powder diffractometer with a copper-K-α radiation source.

The invention will now be described in detail in connection with certain preferred and optional embodiments, so that various aspects thereof may be more fully understood and appreciated.

Thus, there is provided a novel crystalline form of Bictegravir sodium which forms the first aspect of the present invention. The crystalline form is referred to as "Form-C2".

Crystalline Form-C2 may be characterized by having an X-ray powder diffraction spectrum comprising peaks at 5.86, 8.45, 12.32, 18.77 and 25.60±0.2°2θ. The X-ray powder diffraction spectrum may have further peaks at 10.68, 15.92, 21.44 and 24.08±0.2°2θ.

Figure 1:
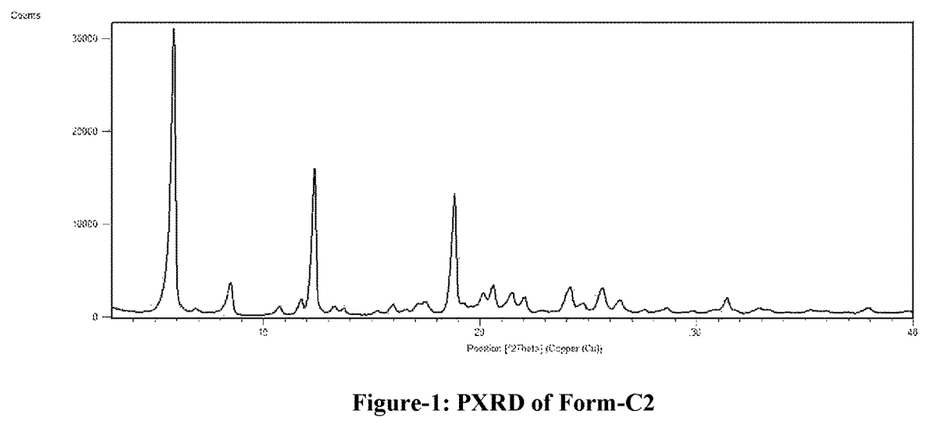
FIG. 1 shows an X-ray powder diffraction of Form-C2 of Bictegravir sodium.

In another embodiment, crystalline Form-C2 of Bictegravir sodium of the present invention is characterized by having an X-ray powder diffraction spectrum as shown in FIG. 1.

The crystalline Form-C2 of Bictegravir sodium can be further characterised by analytical methods including, but not limited to DSC, TGA, IR, NMR, particle size, bulk density, tapped density, flow characteristic, solubility and intrinsic dissolution.

The crystalline Form-C2 of Bictegravir sodium may be characterized by each of the above characteristics alone, and/or by all possible combinations.

In another aspect of the invention, there is proved process for preparation of the crystalline Form-C2 of Bictegravir sodium.

The crystalline Form-C2 of Bictegravir sodium can be prepared by using any other form or a mixture of any forms wherein the Bictegravir is dissolved in a suitable solvent and then treated with an alcoholic solution of sodium wherein the Bictegravir sodium precipitates as a product. The so obtained product is then filtered and dried to get crystalline Form-C2 of Bictegravir sodium.

The Bictegravir base used for the above process, as well as for the following processes, may be in any polymorphic form or in a mixture of any polymorphic forms such as hydrated, solvated, non-solvated or mixture of hydrated, solvated or non-solvated forms thereof.

The starting material can be obtained by any method known in the art, such as the one described in the WO2014100323 which is incorporated herein by reference.

Suitable solvent used in the reaction, as well as for the following processes, is selected from but not limited to the group comprising of alcohols, esters, halogenated hydrocarbons, ketones, hydrocarbons, ethers, nitriles, water, amide, amines or the mixtures thereof.

The alcohol used can be selected from but not limited to aliphatic alcohols such as methanol, ethanol, n-propanol, iso-propanol, n-butanol, iso-butanol, tert-butanol, 1-pentanol, iso-pentanol, propylene glycol and aromatic alcohols such as benzyl alcohol, phenethyl alcohol or the mixtures thereof.

The esters used can be selected from but not limited to ethyl acetate, isopropyl acetate, methyl acetate, benzoate or the mixtures thereof.

The halogenated hydrocarbons used can be selected from but not limited to dichloromethane (MDC), 1,1,1-trichloroethane, 1,2-dichloroethane, 1,1-dichloroethane, chloroform and carbon tetrachloride or the mixtures thereof.

The ketones used can be selected from but not limited to acetone, methyl ethyl ketone, methyl isobutyl ketone, methyl isopropyl ketone or the mixtures thereof.

The hydrocarbons used can be selected from but not limited to hexane, heptane, pentane, cyclohexane, toluene, xylene or the mixtures thereof.

The ethers can be selected from but not limited to 1,4-dioxane, dibutyl ether, diethyl ether, diisoproyl ether, tetrahydrofuran, t-butyl methyl ether or the mixtures thereof.

Preferably, reaction is conducted at a temperature ranging from 25° C. to the reflux temperature of the solvent used.

Preferably, the isolated solids are dried under reduced pressure at 25-100° C., preferably at 40-80° C.; for at about 1 hour to about 30 hours Thus, there is provided a novel crystalline form of Bictegravir sodium which forms the second aspect of the present invention. The crystalline form is referred to as "Form-C3".

Crystalline Form C3 may be characterized by having an X-ray powder diffraction spectrum comprising peaks at 6.54, 12.34, 13.95, 15.82 and 18.60±0.2°2θ.

Figure 2:
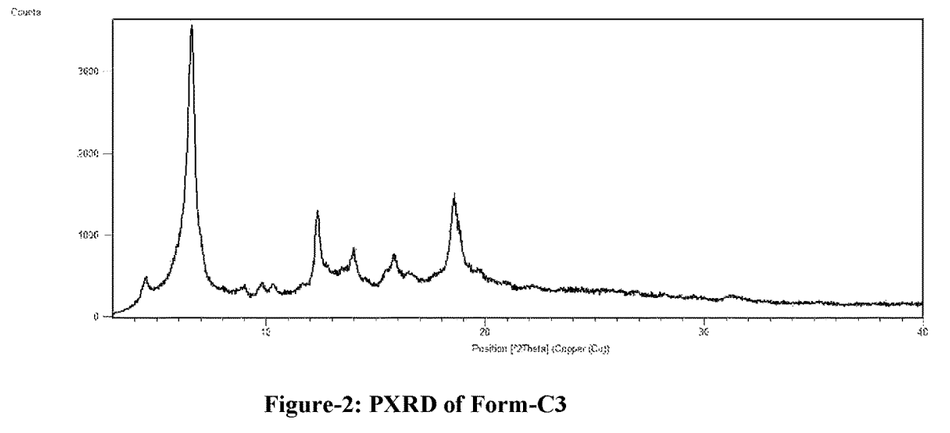
FIG. 2 shows an X-ray powder diffraction of Form-C3 of Bictegravir sodium.

In another embodiment, crystalline Form-C3 of Bictegravir sodium of the present invention is characterized by having an X-ray powder diffraction spectrum as shown in FIG. 2.

The crystalline Form-C3 of Bictegravir sodium can be further characterised by analytical methods including, but not limited to DSC, TGA, IR, NMR, particle size, bulk density, tapped density, flow characteristic, solubility and intrinsic dissolution.

The crystalline Form-C3 of Bictegravir sodium may be characterized by each of the above characteristics alone, and/or by all possible combinations.

In another aspect of the invention, there is proved process for preparation of the crystalline Form-C3 of Bictegravir sodium.

The crystalline Form-C3 of Bictegravir sodium can be prepared by drying the crystalline Form-C2 of Bictegravir sodium for a sufficient time.

Preferably, drying is for a period of about 30 minutes to about 10 hours, preferably of about 1 hour to about 8 hours. Preferably, drying is done at about at about 50° C. to about 180° C., more preferably at 80° C. to about 150° C.

Thus, there is provided a novel crystalline form of Bictegravir sodium which forms the third aspect of the present invention. The crystalline form is referred to as "Form-C4".

Crystalline Form-C4 may be characterized by having an X-ray powder diffraction spectrum comprising peaks at 6.39, 9.00, 15.84, 19.29, 20.87 and 22.44±0.2°2θ.

The X-ray powder diffraction spectrum may have further peaks at 10.94, 12.01, 18.58 and 28.19±0.2°2θ.

Figure 3:
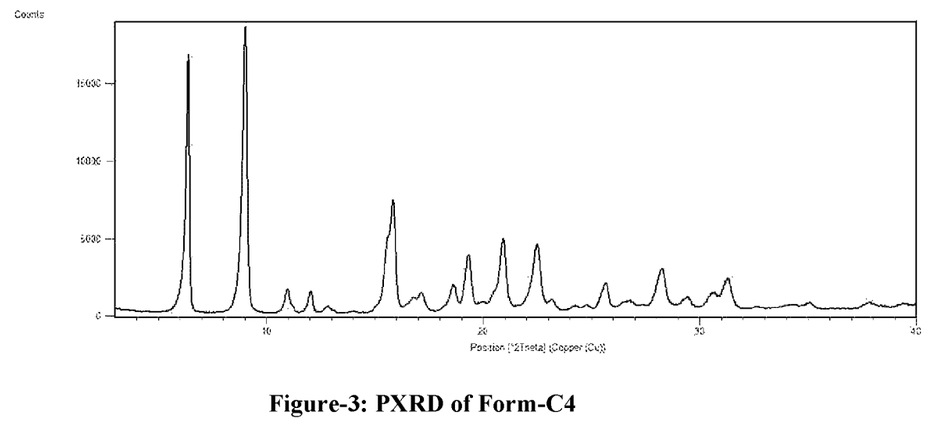
FIG. 3 shows an X-ray powder diffraction of Form-C4 of Bictegravir sodium

In another embodiment, crystalline Form-C4 of Bictegravir sodium of the present invention is characterized by having an X-ray powder diffraction spectrum as shown in FIG. 3.

In another embodiment, crystalline Form-C4 of Bictegravir sodium of the present invention is characterized by Differential Scanning Calorimetry (DSC; evaluation by peak maximum; heating rate: 10° C./min). The value given was determined using a DSC2500 Make: TA instruments.

Figure 5:
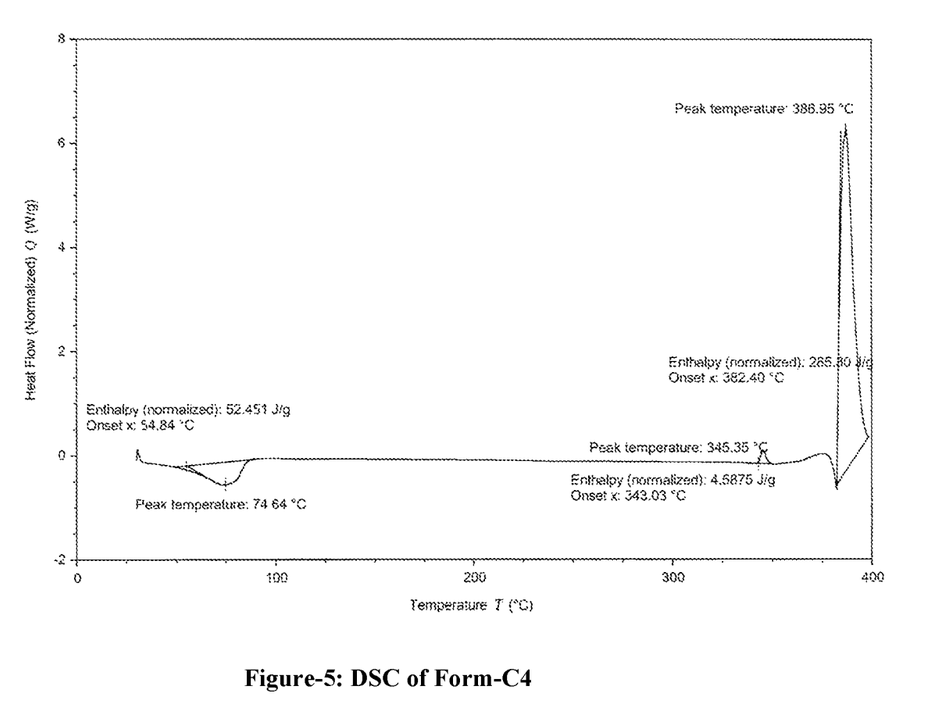
FIG. 5 shows the thermoanalysis and determination of the melting point (DSC) of Form-C4 of Bictegravir sodium

FIG. 5 shows the characteristic differential scanning calorimetry (DSC) curve of the crystalline Form-C4 of Bictegravir sodium. The DSC plot for the sample shows an exotherm with an onset at 343.03° C., a peak maximum at 345.35° C., and an enthalpy change of 4.5875 J/g and a second melting exotherm with an onset at 382.40° C., a peak maximum at 386.95° C., and an enthalpy change of 285.30 J/g.

In yet another embodiment, crystalline Form-C4 of Bictegravir sodium of the present invention is characterized by TGA.

Figure 6:
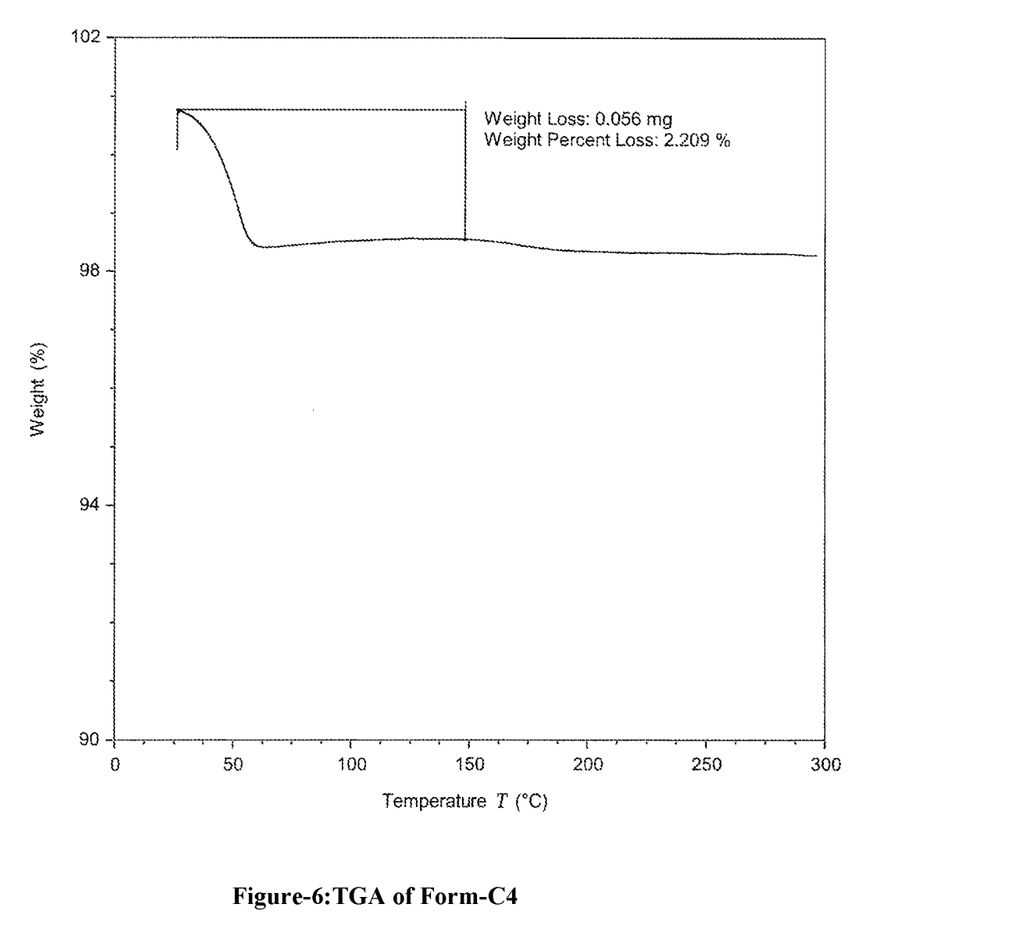
FIG. 6 shows a thermogravimetric analysis (TGA) of Form-C4 of Bictegravir sodium
Figure 7:
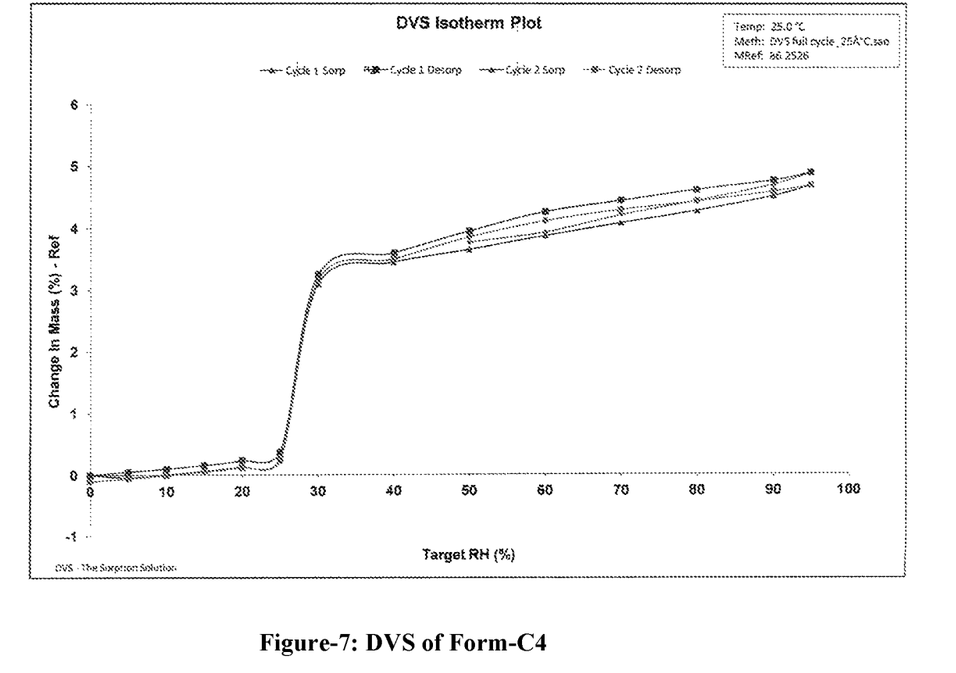
FIG. 7 shows a dynamic vapour sorption (DVS) isotherm of Form-C4 of Bictegravir sodium

FIG. 6 illustrates a simultaneous thermogravimetric/differential thermal analyzer (TGA/DTA) profile of crystalline Form-C4 of Bictegravir sodium, according to one embodiment. For the analysis about 5 mg of crystalline Form-C4 of Bictegravir sodium was weighed into an open aluminum pan and loaded into a simultaneous thermogravimetric/differential thermal analyzer (TGA/DTA) and held at room temperature. The sample was then heated at a rate of 10° C./min from 25° C. to 300° C. during which time the change in sample weight was recorded along with any differential thermal events. Nitrogen was used as the purge gas at a flow rate of 50 ml/min. The TGA/DAT profile of crystalline Form-C4 of Bictegravir sodium shows an initial weight loss of 2.209% between 20° C. to 60° C., also seen as an endotherm in the DTA curve. This weight losses could be loss of moisture from the material. In yet another embodiment, crystalline Form-C4 of Bictegravir sodium of the present invention is characterized by a dynamic vapor sorption (DVS). FIG. 7 illustrates a dynamic vapor sorption (DVS) isotherm profile of crystalline Form-C4 of Bictegravir sodium. For the DVS measurement a sample of crystalline Form-C4 of Bictegravir sodium was cycled through changing humidity conditions to determine its hygroscopicity.

Dynamic Vapour Sorption analysis was performed on DVS Make: Surface Measure System, Model: DVS Intrinsic. Sample was subjected to sorption and desorption analysis (2 cycles) in dm/dt mode with dm/dt value 0.002%/min at 25° C.

Method Steps:
Stabilized at 50% RH for 300 min in time mode.
1-st Cycle Sorption and Desorption:
  Increasing 50% RH to 90% RH (10% RH interval) and from 90% RH to 95% RH (5% RH interval)
  Decreasing 95% RH to 90% RH (5% RH interval), from 90% RH to 30% RH (10% RH interval) and from 30% RH to 5% RH (5% RH interval)
2nd Cycle—Drying at 0% RH for 300 Min in Time Mode:
  Increasing 0% RH to 30% RH (5% RH interval), from 30% RH to 90% RH (10% RH interval) and from 90% RH to 95% RH (5% RH interval)

Decreasing 95% RH to 90% RH (5% RH interval), from 90% RH to 30% RH (10% RH interval) and from 30% RH to 5% RH (5% RH interval)

The crystalline Form-C4 of Bictegravir sodium can be further characterised by analytical methods including, but not limited to, IR, NMR, particle size, bulk density, tapped density, flow characteristic, solubility and intrinsic dissolution.

The crystalline Form-C4 of Bictegravir sodium may be characterized by each of the above characteristics alone, and/or by all possible combinations.

In another aspect of the invention, there is proved process for preparation of the crystalline Form-C4 of Bictegravir sodium.

The crystalline Form-C4 of Bictegravir sodium can be prepared by using any other form or a mixture of any forms, wherein the Bictegravir is dissolved in a suitable solvent and then treated with an alcoholic solution of sodium, wherein the Bictegravir sodium precipitates as a product. The so obtained product is then filtered and dried to get crystalline Form C4 of Bictegravir sodium.

Thus, there is provided a novel crystalline form of Bictegravir sodium which forms the fourth aspect of the present invention. The crystalline form is referred to as "Form-C5".

Crystalline Form-C5 may be characterized by having an X-ray powder diffraction spectrum comprising peaks at 6.48, 7.82, 10.97, 12.82, 16.23 and 19.32±0.2°2θ.

The X-ray powder diffraction spectrum may have further peaks at 11.51, 22.14 and 22.50±0.2°2θ.

Figure 4:
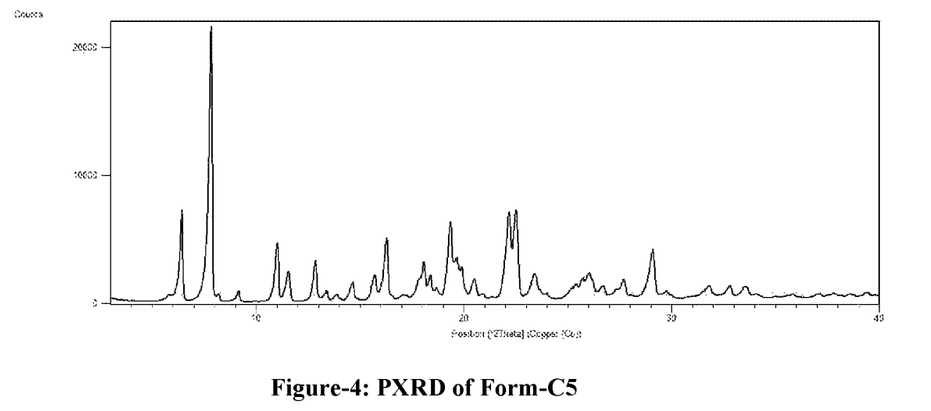
FIG. 4 shows an X-ray powder diffraction of Form-C5 of Bictegravir sodium

In another embodiment, crystalline Form-C5 of Bictegravir sodium of the present invention is characterized by having an X-ray powder diffraction spectrum as shown in FIG. 4.

The crystalline Form-C5 of Bictegravir sodium can be further characterised by analytical methods including, but not limited to DSC, TGA, IR, NMR, particle size, bulk density, tapped density, flow characteristic, solubility and intrinsic dissolution.

The crystalline Form-C5 of Bictegravir sodium may be characterized by each of the above characteristics alone, and/or by all possible combinations.

In another aspect of the invention, there is proved process for preparation of the crystalline Form-C5 of Bictegravir sodium.

The crystalline Form-C5 of Bictegravir sodium can be prepared by using any other form or a mixture of any forms, wherein the Bictegravir is dissolved in a suitable solvent and then treated with an alcoholic solution of sodium wherein the Bictegravir sodium precipitates as a product. The so obtained product is then filtered and dried to get crystalline Form C5 of Bictegravir sodium.

Thus, there is provided a novel crystalline form of Bictegravir sodium which forms the fifth aspect of the present invention. The crystalline form is referred to as "Form-C6".

Crystalline Form-C6 may be characterized by having an X-ray powder diffraction spectrum comprising peaks at 5.63, 11.28, 12.34 and 18.76±0.2°2θ. The X-ray powder diffraction spectrum may have further peaks at 15.36, 17.28, 19.84 and 21.31±0.2°2θ.

Figure 8:
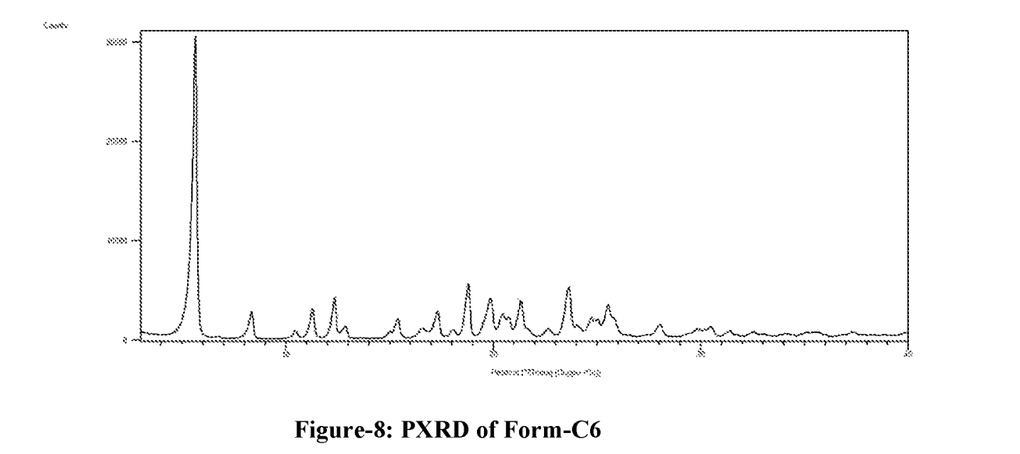
FIG. 8 shows an X-ray powder diffraction of Form-C6 of Bictegravir sodium.

In another embodiment, crystalline Form-C6 of Bictegravir sodium of the present invention is characterized by having an X-ray powder diffraction spectrum as shown in FIG. 8.

The crystalline Form-C6 of Bictegravir sodium can be further characterised by analytical methods including, but not limited to DSC, TGA, IR, NMR, particle size, bulk density, tapped density, flow characteristic, solubility and intrinsic dissolution.

The crystalline Form-C6 of Bictegravir sodium may be characterized by each of the above characteristics alone, and/or by all possible combinations.

In another aspect of the invention, there is proved process for preparation of the crystalline Form-C6 of Bictegravir sodium.

The crystalline Form-C6 of Bictegravir sodium can be prepared by using any other form or a mixture of any forms, wherein the Bictegravir is dissolved in a suitable solvent and then treated with an alcoholic solution of sodium, wherein the Bictegravir sodium precipitates as a product. The so obtained product is then filtered and dried to get crystalline Form C6 of Bictegravir sodium.

Thus, there is provided a novel crystalline form of Bictegravir sodium which forms the sixth aspect of the present invention. The crystalline form is referred to as "Form-C7".

Crystalline Form C7 may be characterized by having an X-ray powder diffraction spectrum comprising peaks at 5.28, 7.75, 10.58, 16.49, 17.12 and 18.64±0.2°2θ.

Figure 9:
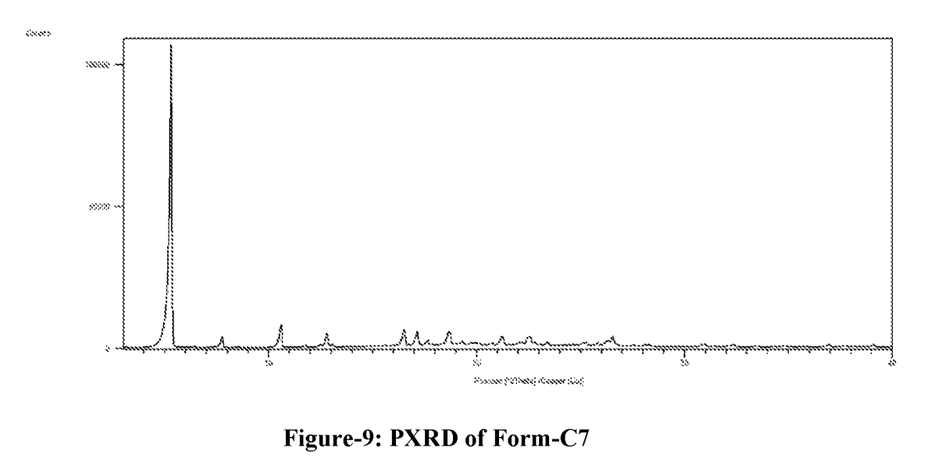
FIG. 9 shows an X-ray powder diffraction of Form-C7 of Bictegravir sodium.

In another embodiment, crystalline Form-C7 of Bictegravir sodium of the present invention is characterized by having an X-ray powder diffraction spectrum as shown in FIG. 9.

The crystalline Form-C7 of Bictegravir sodium can be further characterised by analytical methods including, but not limited to DSC, TGA, IR, NMR, particle size, bulk density, tapped density, flow characteristic, solubility and intrinsic dissolution.

The crystalline Form-C7 of Bictegravir sodium may be characterized by each of the above characteristics alone, and/or by all possible combinations.

In another aspect of the invention, there is proved process for preparation of the crystalline Form-C7 of Bictegravir sodium.

The crystalline Form-C7 of Bictegravir sodium can be prepared by using any other form or a mixture of any forms, wherein the Bictegravir is dissolved in a suitable solvent and then treated with an alcoholic solution of sodium, wherein the Bictegravir sodium precipitates as a product. The so obtained product is then filtered and dried to get crystalline Form C7 of Bictegravir sodium.

Preferably, reaction is conducted at a temperature ranging from 25° C. to the reflux temperature of the solvent used.

Preferably, the isolated solids are dried under reduced pressure at 25-100° C., preferably at 40-80° C.; for at about 1 hour to about 30 hours.

Thus, there is provided a novel crystalline form of Bictegravir sodium which forms the seventh aspect of the present invention. The crystalline form is referred to as "Form-C8".

Crystalline Form-C8 may be characterized by having an X-ray powder diffraction spectrum comprising peaks at 6.49, 7.53, 12.97, 14.56, 18.73, 20.82 and 26.38±0.2°2θ.

Figure 10:
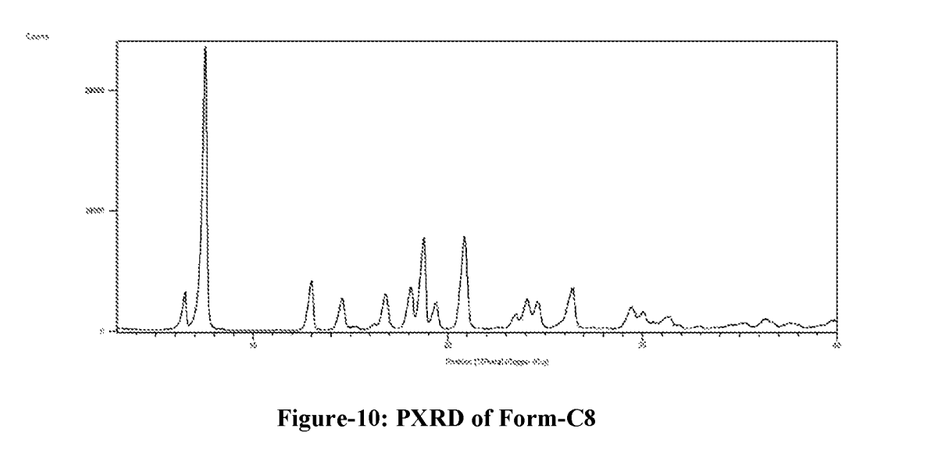
FIG. 10 shows an X-ray powder diffraction of Form-C8 of Bictegravir sodium

In another embodiment, crystalline Form-C8 of Bictegravir sodium of the present invention is characterized by having an X-ray powder diffraction spectrum as shown in FIG. 10.

The crystalline Form-C8 of Bictegravir sodium can be further characterised by analytical methods including, but not limited to DSC, TGA, IR, NMR, particle size, bulk density, tapped density, flow characteristic, solubility and intrinsic dissolution.

The crystalline Form-C8 of Bictegravir sodium may be characterized by each of the above characteristics alone, and/or by all possible combinations.

In another aspect of the invention, there is proved process for preparation of the crystalline Form-C8 of Bictegravir sodium.

The crystalline Form-C8 of Bictegravir sodium can be prepared by stirring Bictegravir sodium in a suitable solvent for a sufficient time and then filtering and drying to get crystalline Form C8 of Bictegravir sodium.

The Bictegravir sodium used for the above process, as well as for the following processes, may be in any polymorphic form or in a mixture of any polymorphic forms such as hydrated, solvated, non-solvated or mixture of hydrated, solvated or non-solvated forms thereof. Preferably, the Bictegravir sodium used for the above process is in the crystalline form. More preferably, the Bictegravir sodium used for the above process is crystalline Form-C7 of Bictegravir sodium.

Preferably, stirring is for a period of about 10 minutes to about 2 hours, preferably of about 15 minutes to about 1.5 hours. Preferably, stirring is done at about at about 20° C. to about 50° C., more preferably at 25° C. to about 40° C.

Preferably, drying is for a period of about 5 minutes to about 60 minutes, preferably of about 10 minutes to about 50 minutes. Preferably, drying is done at about at about 50° C. to about 180° C., more preferably at 80° C. to about 150° C.

Thus, there is provided a novel crystalline form of Bictegravir sodium which forms the eighth aspect of the present invention. The crystalline form is referred to as "Form-C9".

Crystalline Form-C9 may be characterized by having an X-ray powder diffraction spectrum comprising peaks at 6.31, 6.70, 7.77, 13.41, 20.23 and 24.85±0.2°2θ.

Figure 11:
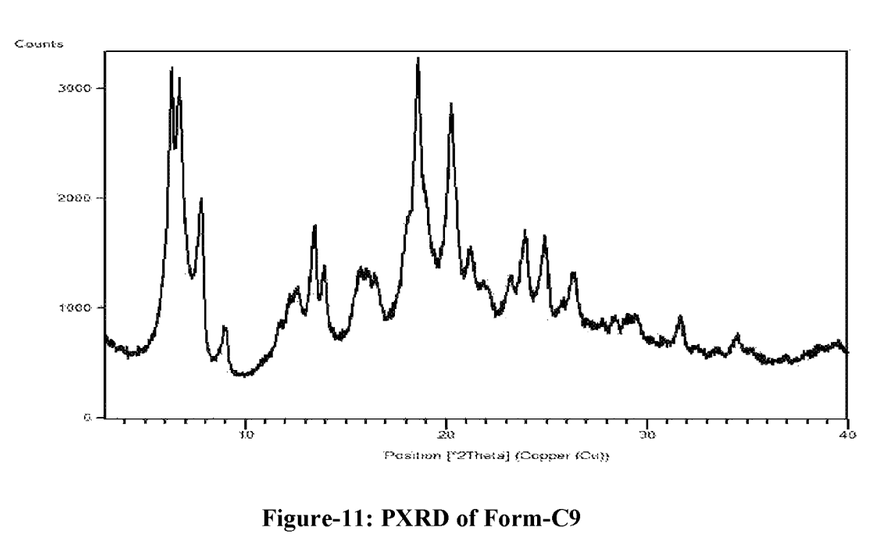
FIG. 11 shows an X-ray powder diffraction of Form-C9 of Bictegravir sodium

In another embodiment, crystalline Form-C9 of Bictegravir sodium of the present invention is characterized by having an X-ray powder diffraction spectrum as shown in FIG. 11.

The crystalline Form-C9 of Bictegravir sodium can be further characterised by analytical methods including, but not limited to DSC, TGA, IR, NMR, particle size, bulk density, tapped density, flow characteristic, solubility and intrinsic dissolution.

The crystalline Form-C9 of Bictegravir sodium may be characterized by each of the above characteristics alone, and/or by all possible combinations.

In another aspect of the invention, there is proved process for preparation of the crystalline Form-C9 of Bictegravir sodium.

The crystalline Form-C9 of Bictegravir sodium can be prepared by drying Bictegravir sodium for a sufficient time.

The Bictegravir sodium used for the above process, as well as for the following processes, may be in any polymorphic form or in a mixture of any polymorphic forms such as hydrated, solvated, non-solvated or mixture of hydrated, solvated or non-solvated forms thereof. Preferably, the Bictegravir sodium used for the above process is in the crystalline form. More preferably, the Bictegravir sodium used for the above process is crystalline Form-C2 of Bictegravir sodium.

Preferably, drying is for a period of about 5 hours to about 40 hours. Preferably drying is performed using different heating rates. Preferably, first drying is done at about at about 30° C. to about 50° C. for about 5 hours to about 10 hours. Preferably, second, drying is done at about at about 50° C. to about 75° C. for about 10 hours to about 15 hours. Preferably, third drying is done at about at about 75° C. to about 90° C. for about 4 hours to about 8 hours.

Having described techniques best suited for producing distinct crystalline Forms 2 to 9 of Bictegravir sodium in a laboratory and industrial setting, those skilled in the art will appreciate that these forms may be accessible by yet other methods.

The novel polymorphic forms of Bictegravir sodium obtained according to the present invention are substantially free from other crystal and non-crystal forms of Bictegravir sodium. "Substantially free" from other forms of Bictegravir sodium shall be understood to mean that the polymorphs of Bictegravir sodium contain less than 10%, preferably less than 5%, of any other forms of Bictegravir sodium and less than 1% of other impurities, water or solvates. Thus, the crystalline forms of Bictegravir sodium prepared according to the present invention contain less than 5% total impurities, preferably less than 3% total impurities. In a particularly preferred embodiment, the crystalline forms of Bictegravir sodium prepared according to the present invention contain less than 1% total impurities.

The processes of invention may be used as a method for purifying any form of Bictegravir, or salts thereof as well as for the preparation of the new polymorphic forms.

According to another aspect of the present invention, there is provided a pharmaceutical composition comprising polymorphic forms of Bictegravir sodium as described above, together with one or more pharmaceutically acceptable excipients. The Bictegravir sodium used in the preparation of pharmaceutical compositions may substantially consist of one of forms C2, C3, C4, C5, C6, C7, C8 or C9 described above, or may substantially consist of a combination of two or more of said forms.

According to yet another aspect of the present invention there is provided use of polymorphic Forms of Bictegravir sodium as described above, in the preparation of a medicament useful in treating or preventing HIV infection.

The invention will now be further described by the following examples, which are illustrative rather than limiting.

EXAMPLES

Example 1

Preparation of Crystalline Form-C2 of Bictegravir Sodium

Bictegravir (5 gm, 11.1261 mmoles) was dissolved in 150 mL of 1-butanol at 50-55° C. To the clear solution was added 10 mL of 5% methanolic sodium hydroxide solution. The reaction mass was stirred for 4 hours at room temperature. The resulting solid was isolated by filtration, dried under vacuum. The isolated solid was identified as crystalline Form-C2 of Bictegravir sodium, by powder X-ray diffraction pattern.

Yield: 5.2 gm

Example 2

Preparation of Crystalline Form-C3 of Bictegravir Sodium

Crystalline Form-C2 of Bictegravir sodium (2.5 g) was dried at 140° C. for about 40-50 minutes. The resulting solid was identified as crystalline Form-C3 of Bictegravir sodium, by powder X-ray diffraction pattern Example 3

Preparation of Crystalline Form-C4 of Bictegravir Sodium

Bictegravir (3 gm,) was dissolved in 15 mL of dichloromethane at room temperature. To the clear solution was added 6 mL of 5% methanolic sodium hydroxide solution. The reaction mass was stirred for 1-2 hours at room temperature. The resulting solid was isolated by filtration, dried under vacuum. The isolated solid was identified as crystalline Form-C4 of Bictegravir sodium, by powder X-ray diffraction pattern.

Yield: 3.1 gm

Example 4

Preparation of Crystalline Form-C5 of Bictegravir Sodium

Bictegravir (0.2 gm,) was dissolved in 2.5 mL of methyl benzoate at room temperature. To the clear solution was added 0.4 mL of 5% methanolic sodium hydroxide solution. The reaction mass was stirred for 18-20 hours at room temperature. The resulting solid was isolated by filtration, dried under vacuum. The isolated solid was identified as crystalline Form-C5 of Bictegravir sodium, by powder X-ray diffraction pattern.

Yield: 0.16 gm

Example 5

Preparation of Crystalline Form-C6 of Bictegravir Sodium

Bictegravir (1.5 g) was dissolved in 75 mL of 1-pentanol at 70° C. temperature. The solution was filtered and to the clear solution was added 3 mL of 5% methanolic sodium hydroxide solution. The reaction mass was stirred for 4-5 hours at room temperature. The resulting solids were isolated by filtration, dried under vacuum at about 50-60° C. for 4-5 hours. The isolated solids were identified as crystalline Form-C6 of Bictegravir sodium, by powder X-ray diffraction pattern.

Yield: 1.2 g

Example 6

Preparation of Crystalline Form-C7 of Bictegravir Sodium

Bictegravir (6.0 g) was dissolved in 40 mL of benzyl alcohol at room temperature. The solution was filtered and to the clear solution was added 12 mL of 5% methanolic sodium hydroxide solution. The reaction mass was stirred for 4-5 hours at room temperature. The resulting solids were isolated by filtration, dried under vacuum at about 50-60° C. for 2-3 hours. The isolated solids were identified as crystalline Form-C7 of Bictegravir sodium, by powder X-ray diffraction pattern.

Yield: 6.5 g

Example 7

Preparation of Crystalline Form-C8 of Bictegravir Sodium

Crystalline Form C7 of Bictegravir sodium (3.0 g) was stirred in 25 mL of ethanol for 15-20 minutes at about 25-30° C. The solids were isolated by filtration, dried under vacuum at about 125-130° C. for 15-20 minutes. The isolated solids were identified as crystalline Form-C8 of Bictegravir sodium, by powder X-ray diffraction pattern.

Yield: 2.1 g

Example 8

Preparation of Crystalline Form-C9 of Bictegravir Sodium

Crystalline Form-C2 of Bictegravir sodium (0.2 g) was dried at about 40-45° C. for about 7-8 hours, followed by at about 70-75° C. for about 12-15 hours, followed by at about 75-80° C. for about 6-8 hours. The resulting solids were identified as crystalline Form-C9 of Bictegravir sodium, by powder X-ray diffraction pattern.

Yield: 0.16 g

We claim:

1. A crystalline Form C4 of bictegravir sodium, characterized by an X-ray powder diffraction spectrum comprising peaks at 6.39, 9.00, 15.84, 19.29, 20.87, and 22.44±0.2° 2θ.

2. The crystalline form of claim 1, further characterized by an X-ray powder diffraction spectrum comprising peaks at 10.94, 12.01, 18.58, and 28.19±0.2° 2θ.

3. The crystalline form of claim 1, having an X-ray powder diffraction spectrum as shown in FIG. 3.

4. The crystalline form of claim 1, further characterized by a DSC showing an exotherm with an onset at 343.03° C., a peak maximum at 345.35° C., and an enthalpy change of 4.5875 J/g and a second melting exotherm with an onset at 382.40° C., a peak maximum at 386.95° C., and an enthalpy change of 285.30 J/g.

5. The crystalline form of claim 1, comprising less than 5% of crystalline polymorphs of bictegravir sodium other than Form C4.

6. A pharmaceutical composition comprising the crystalline form of claim 1.

7. A method of treating an HIV infection in a subject in need thereof, comprising administering to the subject the pharmaceutical composition of claim 6.

8. A method of preparing the crystalline form of claim 1, comprising dissolving bictegravir in a solvent and introducing an alcoholic solution of sodium hydroxide to precipitate bictegravir sodium crystalline Form C4.

9. The method of claim 8, wherein the solvent comprises dichloromethane.

10. The method of claim 8, wherein the alcoholic solution of sodium comprises methanolic sodium hydroxide.

* * * * *